United States Patent [19]

Amplatz et al.

[11] Patent Number: 4,995,866
[45] Date of Patent: Feb. 26, 1991

[54] COMBINED NEEDLE AND DILATOR APPARATUS

[75] Inventors: Kurt Amplatz, St. Paul; Frank Kotula, Maple Grove, both of Minn.

[73] Assignee: Microvena Corporation, Vadnais Heights, Minn.

[21] Appl. No.: 451,093

[22] Filed: Dec. 15, 1989

[51] Int. Cl.$^5$ .............................................. A61M 5/00
[52] U.S. Cl. ....................................... 604/53; 604/166
[58] Field of Search ............... 604/166, 164, 165, 264, 604/272, 280, 53

[56] References Cited

U.S. PATENT DOCUMENTS

| | | |
|---|---|---|
| 3,082,769 | 3/1963 | Palmer ................................ 604/166 |
| 3,388,703 | 6/1968 | Bowes ................................ 604/166 |
| 3,454,006 | 7/1969 | Langdon . |
| 3,492,992 | 2/1970 | Kurtz . |
| 3,565,074 | 2/1971 | Foti . |
| 3,585,986 | 6/1971 | Krug . |
| 3,612,050 | 10/1971 | Sheridan . |
| 4,362,156 | 12/1982 | Feller, Jr. et al. . |
| 4,668,221 | 5/1987 | Luther . |

Primary Examiner—Stephen C. Pellegrino
Attorney, Agent, or Firm—James R. Haller; Gregory P. Kaihoi; Mary P. Bauman

[57] ABSTRACT

The present invention provides a combined needle and dilator comprising a needle having a head with an outer diameter greater than the outer diameter of the body of the needle and a dilating sheath carried about the needle and abutting the rearward needle portion of the needle head. The dilating sheath has a front portion with an outer diameter substantially equal to the outer diameter of the needle head to define, with the head, a generally smooth surface; a body portion with an outer diameter greater than that of the front portion; and a tapered portion disposed between the front and body portions. The tapered portion has an outer surface smoothly merging into the outer surfaces of the front portion and the body portion.

9 Claims, 4 Drawing Sheets

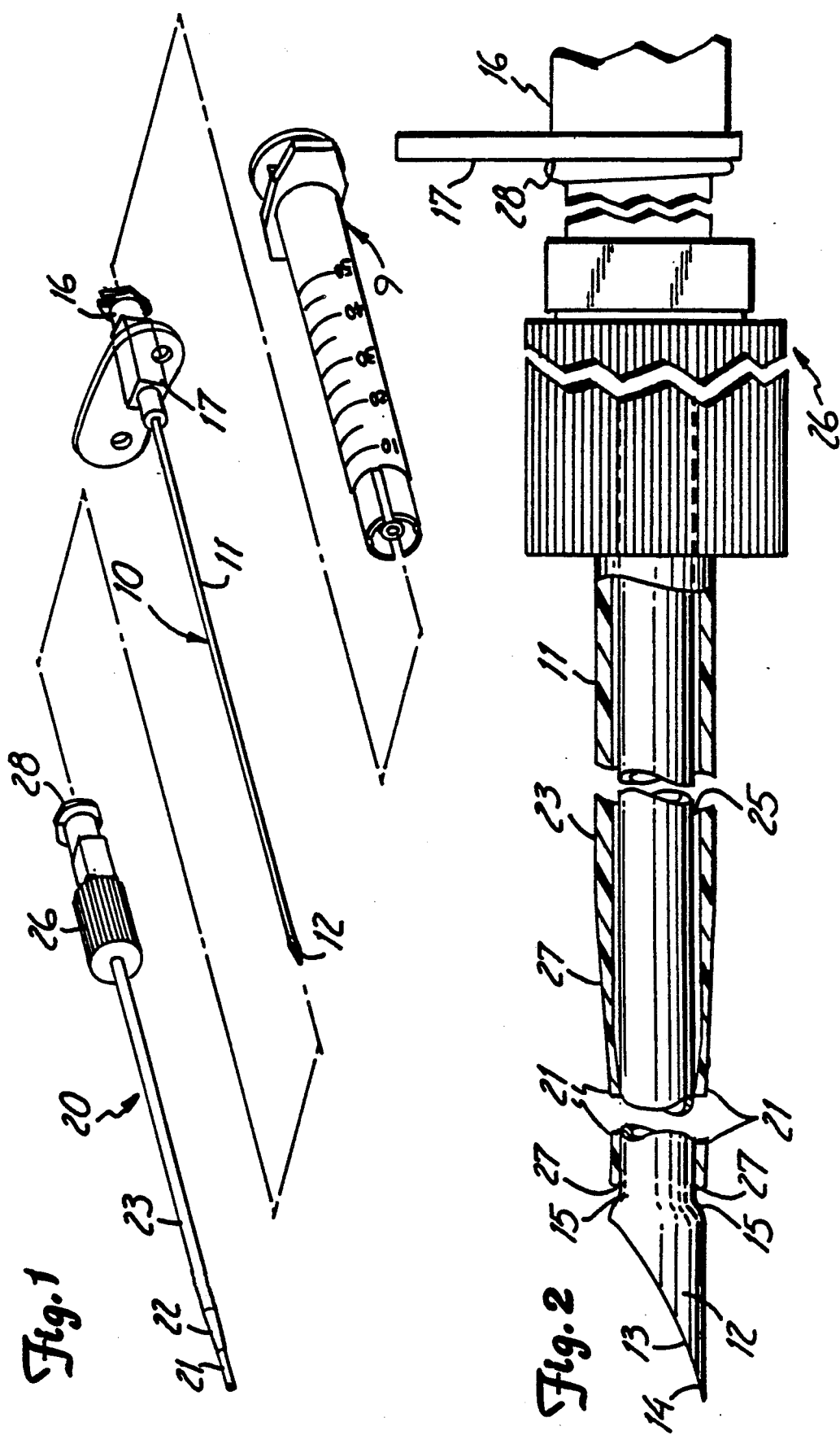

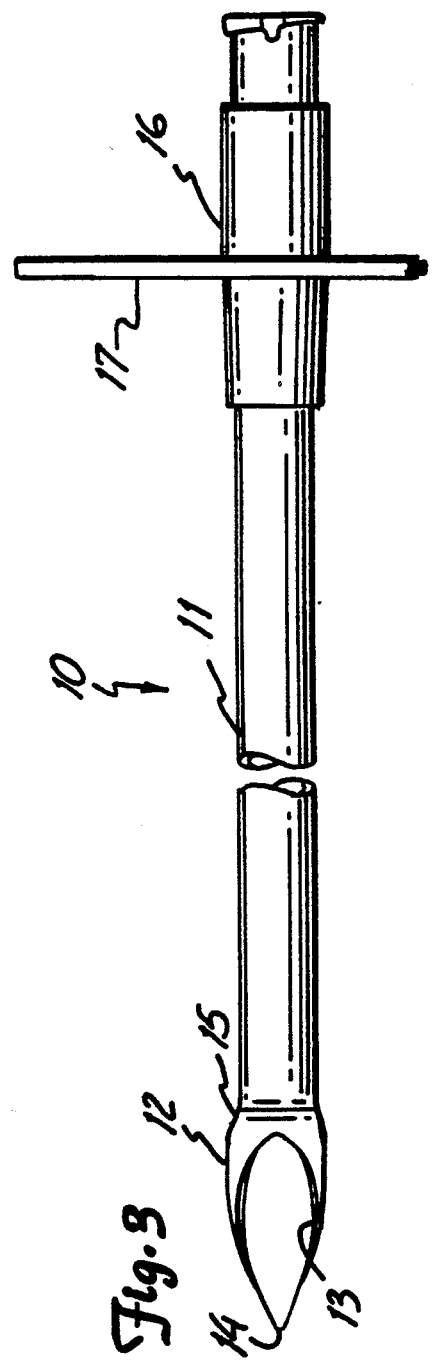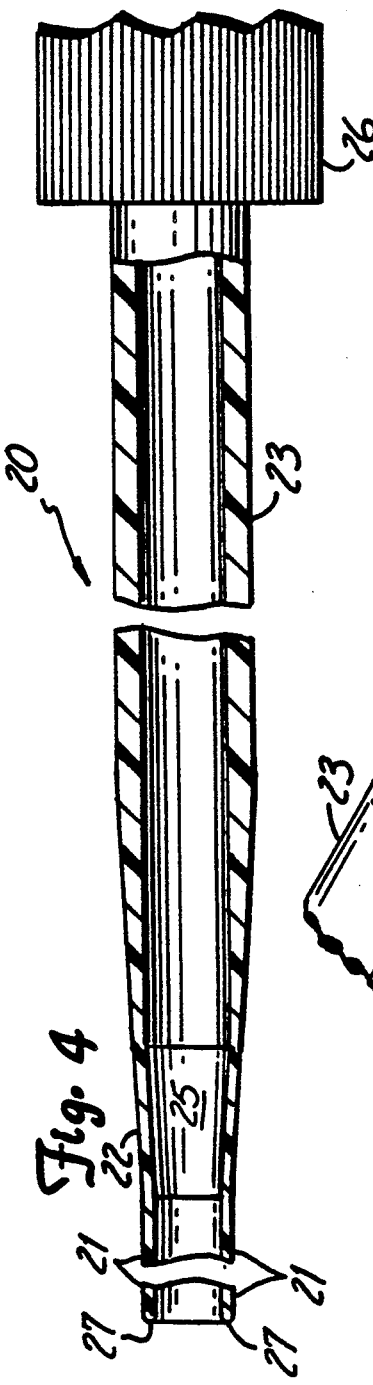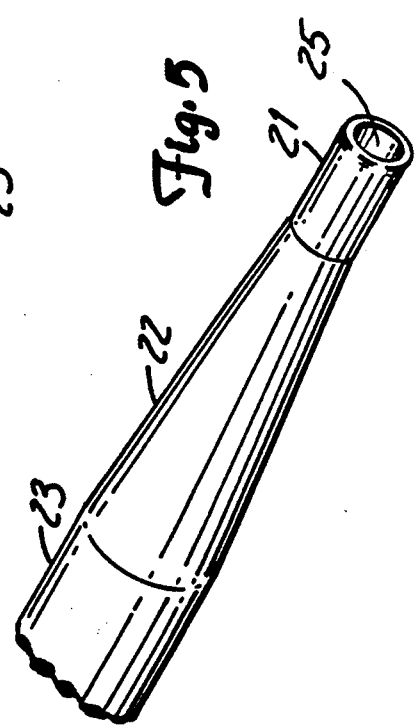

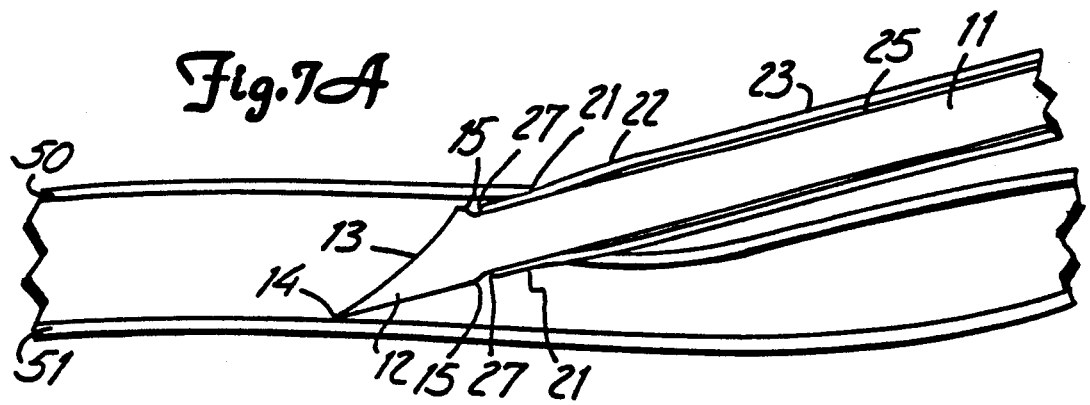
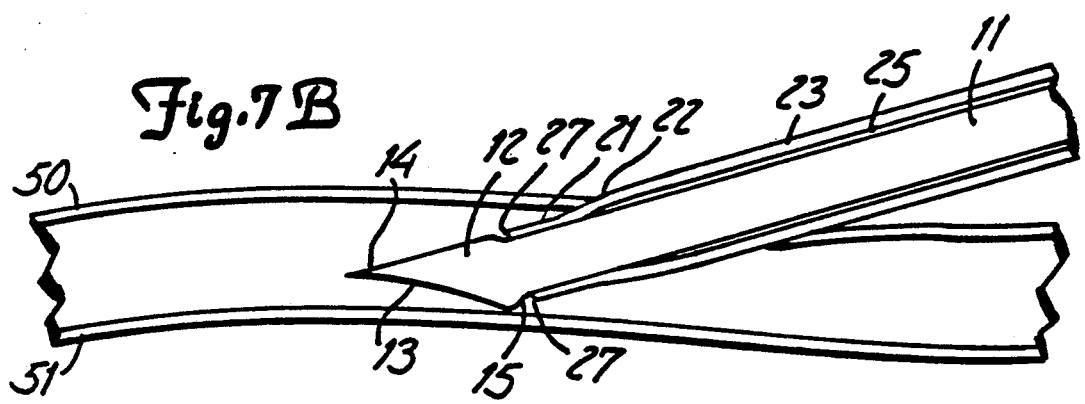
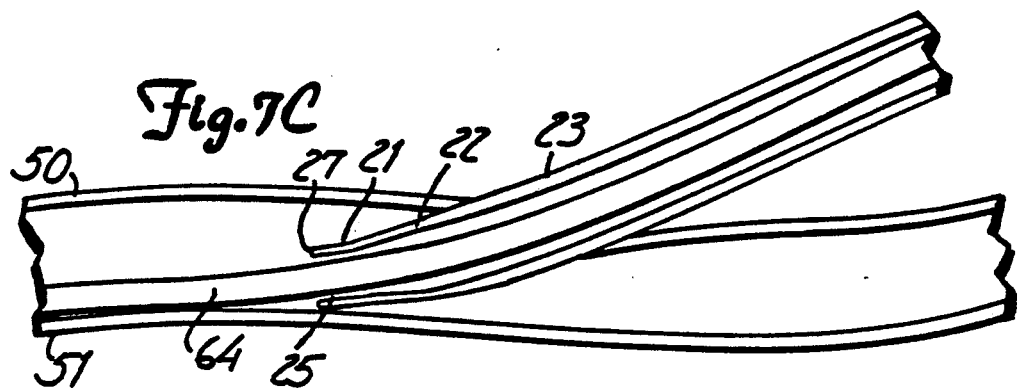

COMBINED NEEDLE AND DILATOR APPARATUS

FIELD OF THE INVENTION

The present invention generally relates to devices for introducing a catheter into a blood vessel. More particularly, this invention relates to an improved apparatus for dilating an opening in a vessel to allow insertion of a catheter.

BACKGROUND OF THE INVENTION

Many of the devices currently commercially available for introducing catheters into the lumen of a blood vessel or other physiological structure are utilized in practicing the Seldinger technique. According to this technique, a wall of the vessel to receive the catheter is pierced by a hypodermic needle, and a flexible guidewire is threaded through the needle into the vessel and is positioned as desired. The needle is then removed and a catheter is inserted over the guide wire into the vein or artery, following the guide wire to the desired position.

A modification of this technique employs a cannula carried by the needle and which enters the vessel with the needle. The guidewire is passed through the needle, leaving the cannula in place about the needle. However, use of such cannulas can result in trauma to both the vessel and the tissue through which the cannula must pass to reach the vessel. The trauma can be reduced by providing a taper on the cannula such that the opening in the vessel is gradually expanded as the cannula is advanced, but such devices (commonly referred to as dilators) as are currently available still cause significant damage as the needle and cannula are passed through the tissue into the vessel. This trauma is primarily due to an abrupt transition in diameter between the dilator and the hollow needle used for cutting a passage through the blood vessel wall. As a hollow needle punctures a vessel, the vessel tends to collapse locally. As the forward shoulder of the dilator contacts the outer wall of the vessel, it cannot simply pass through the hole created by the needle because its outer diameter is greater than that of the needle. Thus, it must be forced through the passageway, damaging tissue as it does so, and pinching the blood vessel walls together. The sharp needle end that extends beyond the end of the dilator thus pierces both vessel walls (rather than only the outer wall) as the dilator forces its way into the vascular channel. In common practice, both walls of the vessel are punctured, the needle then being retracted from the inner wall back into the lumen of the vessel. This causes unnecessary damage to both the blood vessel and surrounding tissue and may cause a hematoma to form below the second puncture; also, the plugs of vascular tissue formed by "coring" as the needle end passes through both vessel walls may tend to plug the lumen of the needle.

Accordingly, it would be desirable to have a needle and dilator assembly which could be used to place the dilator in the lumen of the vessel without necessitating puncture of both the outer and inner vessel walls to guarantee proper placement. Further, it would be desirable to have a device which would allow smooth and relatively atraumatic entry of the dilator into the vascular channel and in which little damage is cased by the tissue in its path.

BRIEF DESCRIPTION OF THE DRAWINGS

FIG. 1 is an exploded perspective view of the combined needle and dilator apparatus of the invention;

FIG. 2 is a broken away view in partial cross-section of the apparatus of FIG. 1 as assembled;

FIG. 3 is a top view of a hollow needle that may be used in the device of FIG. 1;

FIG. 4 is a cross-sectional view of the dilating sheath shown in the device of FIG. 1;

FIG. 5 is a perspective view of the forward end of the dilating sheath of FIG. 4;

FIGS. 7A-7C show sequentially and schematically how a combined needle and dilator apparatus of the invention may be introduced to the blood vessel of a patient.

DETAILED DESCRIPTION OF THE INVENTION

Figure 6A:
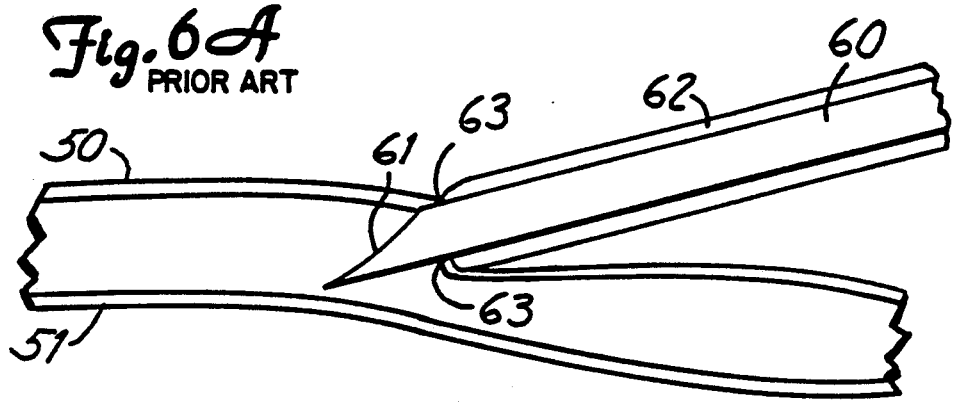
FIGS. 6A-6D show sequentially and schematically how a prior art device is inserted into the blood vessel of a patient.

As best seen in FIG. 1, a combined needle and dilator apparatus according to the present invention includes a hollow needle (10), a dilating sheath (20), and desirably a syringe (9) or other device of similar function which may serve as a handle to orient the needle and sheath. The dilating sheath is designed to be slidably retained over the hollow needle, and the apparatus comprising the sheath and needle is inserted into the patient's blood vessel as a single unit, as will be described in more detail below.

Referring to FIG. 3, the hollow needle includes a hollow shaft (11) having at its forward end a head (12) with a cutting edge (13). The shaft comprises a hollow, substantially cylindrical tube which may be of any useful length, but commonly is between about 3 and about 30 cm in length. The head portion is integrally formed with the shaft at the proximal or forward end thereof and has an outer diameter greater than that of the adjacent shaft. The transition from the outer diameter of the shaft to that of the head creates a generally rearwardly facing shoulder (15). This shoulder can be formed as a taper between the two dimensions substantially as shown, or may provide a much more abrupt transition by being angled sharply outward from the shaft. The head may be formed by any desired method, such as by expanding the diameter of a portion of a shaft of uniform diameter. The cutting edge (13), which includes a piercing tip (14), is suitably ground or otherwise formed at the proximal end of the hollow needle (10). The cutting edge preferably has a curved profile (as shown in FIG. 2) to increase the sharpness of the piercing tip, but may take any desired profile.

The hollow needle may also include an end connector (16) of common design, such as a bayonet connector, provided at its distal end for connection to the hypodermic syringe or other device to support the needle and to block the end of the needle to prevent the loss of more than a minor amount of blood. In a preferred embodiment, a syringe, (9 in FIG. 1) is attached to the end connector to perform this blocking function. A syringe allows the surgeon or other person using the apparatus to see blood as it enters the syringe, indicating that the needle is in the vessel.

A dilating sheath (20) according to the invention is shown in FIGS. 4 and 5. The sheath includes a forward portion (21) which is substantially cylindrical and has an inner diameter at its forward end approximately equal to the outer diameter of the shaft (11) of the needle adjacent the head and an outer diameter substantially equal to the outer diameter of the head (12) of the needle. The sheath also includes a body portion (23) of substantially cylindrical shape and coaxial with the forward portion. The inner diameter of the body portion (23) is greater than that of the forward portion (21) and is desirably only slightly less than the outer diameter of the head of the needle so the needle may be passed through the body portion without undue resistance. The outer diameter of the body portion (23) is determined by the desired size of the passageway to be formed in the vessel wall which in turn depends upon the device to be inserted into the opening after the dilating sheath is removed. Although the body portion outer diameter will vary with the medical procedure being performed, it commonly falls between about 0.026 and 0.120 inches. The forward portion (21) of the sheath has a length equal to at least about five times the outer diameter of the needle shaft.

The sheath also includes a tapered portion (22) disposed between the front portion (21) and the body portion (23) and which has an outer surface that provides a smooth transition between the outer diameters of the front and body portions. The length of the tapered portion is chosen to ensure that the increase in diameter is gradual enough to minimize trauma to the tissue and vessel wall as the opening therein is dilated; as a practical matter, it is preferred that the tapered portion be at least one centimeter in length. The transition between the inner diameter of the body portion (which is preferably only slightly less than the outer diameter of the head of the needle) and the inner diameter of the front portion (which is preferably substantially equal to or slightly larger than the diameter of the shaft of the needle) may be gradual as shown in FIG. 4, or, if so desired for manufacturing ease, may occur more abruptly.

The dilating sheath (20) may also include a mounting means (26) attached to the distal end of the body portion received over the needle and may mate with the end connector (16) thereof. The mounting means (26) can be used to guide the head of the needle into the sheath and also aids in achieving consistent longitudinal placement of the sheath on the needle. The mounting means (26) and connector (16) have confronting surfaces limiting the forward extension of the needle through the sheath to the position shown in FIG. 2. Additionally, the mounting means may also provide a connection to a blocking device such as the syringe (9) mentioned above to prevent loss of blood through the sheath after the needle is removed.

Thus, each of the elements of the dilating sheath are of a hollow, generally tubular construction. This provides the sheath with an axial channel (25) of substantially circular cross section through which the needle (10) may be passed. Since the head (11) of the needle has an outer diameter greater than the inner diameter of the forward portion, the sheath is preferably formed of an elastic material, such as poly(tetrafluoroethylene), which would allow its front portion (27) to expand sufficiently to allow the head to pass therethrough. Once the rearwardly facing shoulder (15) is passed forward through the proximal end of the forward sheath portion (as the device is assembled), the front portion may contract to its original dimensions wherein its inner diameter is substantially equal to the outer diameter of the needle's shaft, providing a snug fit of this part of the sheath about the needle. As the forward portion so contracts, a distinct "pop" may be felt, allowing the person using the apparatus to readily determine when the needle has passed through the sheath during assembly. The end (27) of the sheath may have a small, inwardly protruding annular "lip" or "rim" (not shown) that snugly engages the shaft of the needle rearwardly of the head.

The sheath should be as long as or slightly shorter than the length of the hollow shaft (11) of the needle to place the proximal end (27) of the front portion of the sheath on the shaft of the needle in a position immediately adjacent or abutting the shoulder (15), as shown in FIG. 2, the respective confronting surfaces (28) and (17) of the sheath and needle preventing the sheath from relative rearward movement from that position.

As mentioned above, the outer diameter of the forward sheath portion is substantially equal to or slightly greater than the outer diameter of the head. Retaining the proximal end (27) of the front portion at a position immediately behind the head thus presents a relatively smooth outer surface of the apparatus comprising the combination of the needle and the sheath. The proximal end (27) is preferably rounded rather than blunt to minimize any trauma which may result when inserting the apparatus into the patient due to the slight discontinuity in the outer surface at the interface between the sheath and the shoulder (15).

By way of example, in one preferred embodiment wherein the dilating sheath provides a size 6.0 French dilator, the shaft (11) of the needle has an outer diameter of approximately 0.042 inches and the outer diameter of the head (12) of the needle is approximately 0.048 inches. The inner diameter of the body portion (23) of the sheath is approximately 0.045 inches, or only 0.003 inches less than the outer diameter of the needle's head. The inner diameter of the forward portion (21) of the sheath is approximately 0.042 inches, i.e., substantially the same as the outer diameter of the shaft of the needle. The outer diameter of the forward sheath portion (21) is approximately 0.048 inches, i.e., substantially equal to the outer diameter of the head of the needle. The outer diameter of the body portion of the sheath in this embodiment is approximately 0.079 inches, meaning that the tapered portion must increase approximately 0.031 inches in outer diameter between its proximal end that is joined to the forward portion and its distal end that is joined to the body portion. The forward portion (21) has a uniform diameter and is preferably between about three and ten millimeters in length, most preferably about five millimeters in length. The length of the front and tapered portions together measure preferably at least 20 millimeters to ensure that the increase in outer diameter is gradual and minimizes damage to tissue as the apparatus enters the patient. The length of the head of the needle from the beginning of the shoulder (15) to the piercing tip (14) will depend upon the design of the cutting edge (13), but may be approximately four millimeters. This exemplary embodiment therefore provides a combined needle and dilator apparatus with a substantially smooth outer surface comprising the head of the needle and the front portion of the sheath with an outer diameter of approximately 0.048 inches, a gradual increase in diameter between 0.048 inches and the desired passage width of about 0.079 inches, and an extended portion with an outer diameter of 0.079 inches.

Figure 6B:
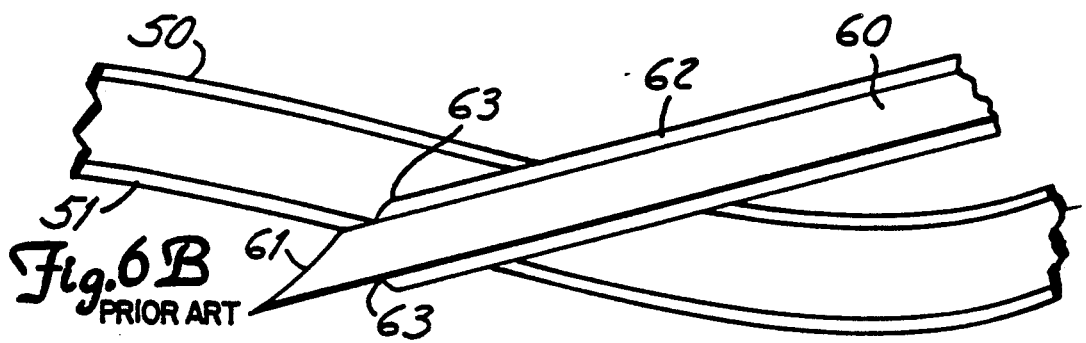

FIGS. 6A–6D show a prior art device and a common method of placing the sheath thereof in the lumen of a blood vessel. The device includes a hollow needle (60) of uniform diameter length with a sharpened cutting edge (61) at its proximal end. A sheath (62) is carried about the needle at a position disposed behind the cutting edge and has a relatively blunt end. Thus, the proximal end of the sheath provides a forwardly facing shoulder 63. In practice, the cutting edge (61) of the needle punctures a hole through the outer wall of the vessel (50), i.e., that wall of the vessel closest to the skin. The puncture tends to cause the vessel to partially collapse locally. As the needle is advanced, the shoulder (63) presses against the outer wall of the collapsed vessel without gaining entry thereto (see FIG. 6A). There is no clear indication to the operator as to when both the needle and the sheath are in the lumen of the vessel. In order to ensure that the sheath has worked its way through the outer wall, the needle is driven through the inner wall (51) of the vessel which is supported by underlying tissue, as shown in FIG. 6B.

Figure 6C:
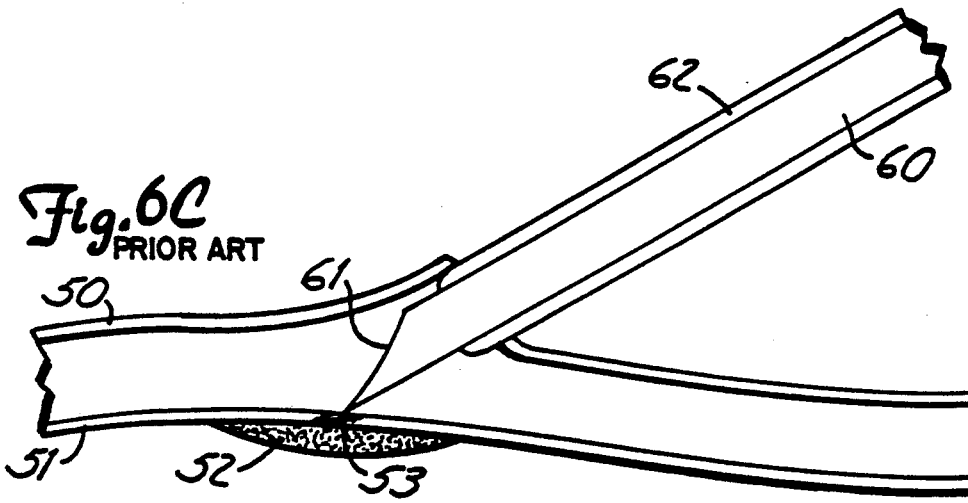
Figure 6D:
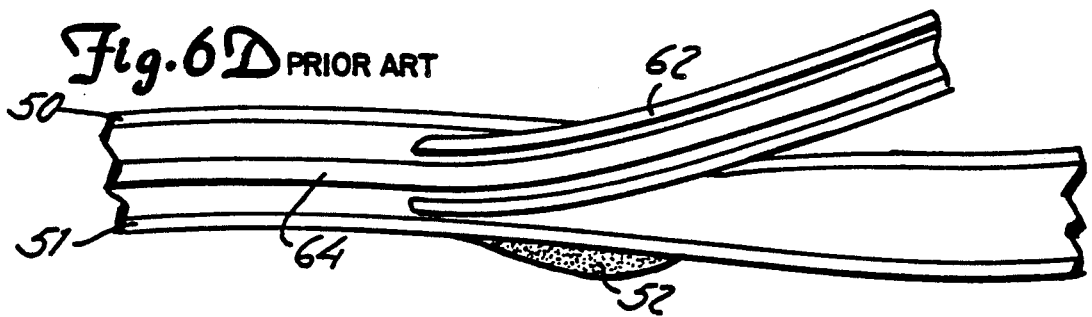

The needle is then partially retracted to place the proximal end of the needle and the sheath in the lumen of the vessel. However, as shown in FIG. 6C, this traumatizes the vessel and surrounding tissue in several ways. Obviously, driving the needle through the inner wall leaves a hole therein, and this puncture wound serves no useful purpose in any of the subsequent operations described below. The tissue beneath the inner wall is also damaged by the puncture, and a hematoma (52) may form therein. This procedure may also traumatize the area surrounding the point of entry of the apparatus by pulling the outer wall of the vessel and surrounding tissue along with the sheath as it is retracted.

Once the proximal end of the sheath is in the lumen of the vessel, a guidewire (64) is passed through the sheath into the vein or artery, and serves to guide a subsequently inserted catheter.

FIGS. 7A–C depict a method of using a device according to the invention in sequential fashion. After the puncture site has been prepared, as by sterilization, the combined needle and dilator apparatus is passed through the outlying tissue and the outer wall (50) into the lumen of the vessel, which may be indicated visually by passage of blood through the needle and into the forward portion of the syringe. Referring to FIG. 7A, the apparatus is desirably advanced far enough to place at least a segment of the front portion (21) of the sheath inside the vessel, but care should be taken to avoid piercing inner wall (51) by the piercing tip (14) of the needle. The puncture occurs at an oblique angle to the blood vessel to increase the distance along the axis of the apparatus between the inner and outer walls, and so entering the vessel also allows the sheath to be advanced into the vessel without being blocked by the inner wall. As mentioned above, the head of the needle and the front portion of the sheath are of substantially equal outer diameter, thus together presenting a generally smooth surface so that the proximal end (27) of the sheath does not catch on the skin or outer vascular wall but rather readily enters the lumen of the vessel. That is, the juncture of the head with the forward end of the sheath is sufficiently smooth and continuous as to slide smoothly through the vascular wall. This avoids the necessity of piercing the inner wall with the needle to ensure that the sheath has passed through the outer wall, which in turn avoids trauma associated with the "double puncture" method described above.

Next, the apparatus is preferably turned about its axis approximately 180 degrees to orient the piercing tip away from the inner wall, as shown in FIG. 7B. This step disposes that portion (18) of the head (12) of the needle with the shortest axial length toward the inner wall and allows the apparatus to be further advanced until the head of the needle is again near the inner wall. The needle is then held stationary and the sheath is advanced forwardly over the needle head (12) so that the tapered portion (22) of the sheath enters and begins to dilate the opening in the outer vascular wall. Desirably, the body portion of the sheath with the larger inner diameter also enters the outer wall of the vessel. Once the sheath has entered the lumen of the vessel a short distance, a guide wire may be passed through the needle in the vein or artery. The needle may then be retracted from the vessel and pulled out of the sheath through its distal end. Since the head of the needle may be of slightly greater outer diameter than the inner diameter of the sheath, removal of the needle causes the sheath to locally expand slightly, and the continuous smooth and gentle contact of the needle head with the inner wall of the sheath as the needle passes rearwardly avoids abrupt movement of either the needle or sheath. If a portion of the sheath with an expanded inner diameter has entered the vein or artery, though, this expansion due to the passage of the head of the needle through the sheath is minimized and will not traumatize the wall of the vessel or surrounding tissue. Once the needle has been removed from the sheath, the sheath may be advanced farther along the guidewire into the vessel to a point wherein the body portion of the sheath enters the lumen of the vessel. In this manner, the opening in the tissue and outer wall are fully expanded to the desired diameter. The sheath may then be removed, and a catheter or other medical device may be passed over the guidewire into the vessel as described above.

While a preferred embodiment of the invention has been described, it should be understood that various changes and modifications may be made therein without departing from the spirit of the invention and the scope of the appended claims.

What is claimed is:

1. A combined needle and dilator apparatus, comprising:
    a. A needle with an elongated shaft terminating forwardly in a head having an outer diameter greater than the outer diameter of the shaft adjacent the head and defining a generally rearwardly facing shoulder, the head terminating forwardly in a cutting edge; and
    b. A dilating sheath slidably carried about the needle shaft and having a generally cylindrical front portion terminating in a forward rim abutting the shoulder of the needle head, said front portion having a uniform outer diameter substantially equal to the outer diameter of the needle head to define, with the head, a generally smooth surface; the sheath further having a generally cylindrical body portion with an outer diameter greater than the outer diameter of said front portion, and a tapered portion having rearwardly divergent walls and disposed between said front portion and said body portion of the sheath, the tapered portion having an outer surface smoothly merging into the outer surfaces of the front portion and the body portion.

2. The combined needle and dilator apparatus of claim 1 wherein said tapered portion is at least one centimeter in length.

3. The combined needle and dilator apparatus of claim 1 wherein said front portion is at least about three, but no more than about ten centimeters in length.

4. The combined needle and dilator apparatus of claim 1 wherein said front and tapered portions of the sheath have a combined length of at least two centimeters.

5. The combined needle and dilator apparatus claim 1 wherein the inner diameter of the front portion of the sheath is substantially the same as the outer diameter of the shaft of said needle adjacent the head.

6. The combined needle and dilator apparatus of claim 1 including a hypodermic syringe comprising a barrel and plunger, the barrel having a connector at its forward end, the needle having at its rearward end a connector lockingly engaging the connector of the barrel.

7. The combined needle and dilator apparatus of claim 1 wherein the shaft of the needle is of uniform outer diameter rearwardly of the head.

8. The combined needle and dilator apparatus of claim 1 wherein said needle is hollow and said shaft of said needle comprises a generally hollow tube of uniform diameter.

9. Venipuncture method for vascular introduction of a catheter, including the steps of:
 a. Providing the combined needle and dilator apparatus of claim 1;
 b. Piercing the outer wall of a blood vessel with the cutting edge of the needle head to form a port in the outer wall;
 c. Advancing said apparatus into the vessel until a portion of said sheath enters the lumen of said vessel;
 d. Passing a guidewire through the sheath;
 e. Slidably advancing said sheath over the head of the needle while maintaining said needle in a stationary position;
 f. Slidably retracting said needle from said sheath;
 g. Advancing the tapered portion of the sheath into the vessel to thereby enlarge the port therein;
 h. Removing the sheath from the vessel; and
 i. Passing a catheter over the guidewire and through the port in the outer wall of said vessel.

* * * * *